(12) United States Patent
Hibner et al.

(10) Patent No.: US 7,611,474 B2
(45) Date of Patent: Nov. 3, 2009

(54) CORE SAMPLING BIOPSY DEVICE WITH SHORT COUPLED MRI-COMPATIBLE DRIVER

(75) Inventors: John A. Hibner, Mason, OH (US); Kevin D. Predmore, Heath, OH (US); Lawrence Bullen, Centerburg, OH (US); Vincent J. Contini, Powell, OH (US); James E. Dvorsky, Norwich Township, OH (US); Eric R. Navin, Columbus, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 183 days.

(21) Appl. No.: 11/025,556

(22) Filed: Dec. 29, 2004

(65) Prior Publication Data
US 2006/0149163 A1    Jul. 6, 2006

(51) Int. Cl.
*A61B 10/00* (2006.01)
(52) U.S. Cl. .................. 600/566; 600/564; 600/567; 606/167
(58) Field of Classification Search .......... 600/562, 600/564–568; 606/167, 171, 180
See application file for complete search history.

(56) References Cited

U.S. PATENT DOCUMENTS

| 4,980,545 | A | | 12/1990 | Seki et al. | |
|---|---|---|---|---|---|
| 5,290,303 | A | | 3/1994 | Pingleton et al. | |
| 5,775,333 | A | * | 7/1998 | Burbank et al. | 600/567 |
| 5,928,164 | A | * | 7/1999 | Burbank et al. | 600/567 |
| 5,980,545 | A | * | 11/1999 | Pacala et al. | 606/170 |
| 6,086,543 | A | * | 7/2000 | Anderson et al. | 600/567 |
| 6,086,544 | A | * | 7/2000 | Hibner et al. | 600/568 |
| 6,171,325 | B1 | | 1/2001 | Mauze et al. | |
| 6,238,355 | B1 | * | 5/2001 | Daum | 600/567 |
| 6,273,862 | B1 | | 8/2001 | Privitera et al. | |
| 6,436,054 | B1 | * | 8/2002 | Viola et al. | 600/562 |
| 6,638,235 | B2 | * | 10/2003 | Miller et al. | 600/566 |
| 6,675,037 | B1 | * | 1/2004 | Tsekos | 600/417 |

(Continued)

FOREIGN PATENT DOCUMENTS

WO    WO 2004/052212    6/2004

OTHER PUBLICATIONS

EPO Search Report, Application No. 05258079.2, Mar. 28, 2006, pp. 1-5.

*Primary Examiner*—Max Hindenburg
*Assistant Examiner*—Jonathan M. Foreman
(74) *Attorney, Agent, or Firm*—Frost Brown Todd LLC

(57) ABSTRACT

A core sampling biopsy device is compatible with use in a Magnetic Resonance Imaging (MRI) environment by being driven by either a pneumatic rotary motor or a piezoelectric drive motor. The core sampling biopsy device obtains a tissue sample, such as a breast tissue biopsy sample, for diagnostic or therapeutic purposes. The biopsy device may include an outer cannula having a distal piercing tip, a cutter lumen, a side tissue port communicating with the cutter lumen, and at least one fluid passageway disposed distally of the side tissue port. The inner cutter may be advanced in the cutter lumen past the side tissue port to sever a tissue sample. A cutter drive assembly maintains a fixed gear ratio relationship between a cutter rotation speed and translation speed of the inner cutter regardless of the density of the tissue encountered to yield consistent sample size.

16 Claims, 6 Drawing Sheets

U.S. PATENT DOCUMENTS

| | | |
|---|---|---|
| 6,758,824 B1 | 7/2004 | Miller et al. |
| 6,860,860 B2 * | 3/2005 | Viola .......................... 600/564 |
| 2002/0042581 A1 * | 4/2002 | Cervi .......................... 600/567 |
| 2003/0069517 A1 * | 4/2003 | Stephens et al. ............ 600/568 |
| 2003/0083684 A1 * | 5/2003 | Cesarini et al. ............. 606/170 |
| 2003/0199753 A1 | 10/2003 | Hibner et al. |
| 2003/0199754 A1 | 10/2003 | Hibner et al. |
| 2004/0153003 A1 * | 8/2004 | Cicenas et al. .............. 600/564 |

* cited by examiner

CORE SAMPLING BIOPSY DEVICE WITH SHORT COUPLED MRI-COMPATIBLE DRIVER

FIELD OF THE INVENTION

The present invention relates in general to biopsy devices, and more particularly to biopsy devices having a cutter for severing tissue.

BACKGROUND OF THE INVENTION

The diagnosis and treatment of patients with cancerous tumors, pre-malignant conditions, and other disorders has long been an area of intense investigation. Non-invasive methods for examining tissue include: palpation, X-ray imaging, magnetic resonance imaging (MRI), computed tomography (CT), and ultrasound imaging. When a physician suspects that tissue may contain cancerous cells, a biopsy may be done using either an open procedure or a percutaneous procedure. For an open procedure, a scalpel is used to create a large incision to provide direct visualization of and access to the tissue mass of interest. The entire mass (excisional biopsy) or a part of the mass (incisional biopsy) may then be removed. In percutaneous biopsy procedures, a needle-shaped instrument is inserted through a small incision to access the tissue mass of interest and obtain a tissue sample for later examination and analysis.

Aspiration and core sampling are two percutaneous methods for obtaining tissue from within the body. In an aspiration procedure, tissue is fragmented into pieces and drawn through a fine needle in a fluid medium. The aspiration method is less intrusive than most other sampling techniques, however, it has limited application since the structure of tissue excised by aspiration is destroyed, leaving only individual cells for analysis. In core biopsy, a core or fragment of tissue is obtained in a manner that preserves both the individual cell and the tissue structure for histological examination. The type of biopsy used depends on various factors, no single procedure is ideal for all cases.

A biopsy instrument now marketed under the tradename MAMMOTOME™ is commercially available from Ethicon Endo-Surgery, Inc. for use in obtaining breast biopsy samples, such as described in U.S. patent application No. 2003/0199753, published Oct. 23, 2003 to Hibner et al., which is hereby incorporated by reference in its entirety. The MAMMOTOME™ biopsy instrument is adapted to obtain multiple tissue samples from a patient with only one percutaneous insertion of a piercing element or piercer into the patient's breast. An operator uses the MAMMOTOME™ biopsy instrument to "actively" capture (using vacuum) tissue prior to severing it from surrounding tissue. Tissue is drawn into a lateral port at the distal end of the piercer by a remotely actuated vacuum system. Once the tissue is in the lateral port, a cutter is rotated and advanced through a lumen of the piercer past the lateral port. As the cutter advances past the lateral port opening, it severs the tissue in the port from the surrounding tissue. When the cutter retracts, it pulls the tissue with it and deposits the tissue sample outside of the patient's body.

This version of the MAMMOTOME™ core sampling biopsy instrument is advantageously compatible with use in a Magnetic Resonance Imaging (MRI) system. In particular, ferrous materials are avoided in the instrument so that the strong magnetic field of the MRI system does not attract the instrument. In addition, materials and circuitry are chosen to avoid artifacts in the MRI image by not interfering with the weak RF fields emanated by the tissue being examined. In particular, a control console that is remotely placed from the instrument provides the vacuum, cutter motor control, and graphical user interface. Thus, a flexible driveshaft couples the rotational motions for cutter translation and rotation.

While such an instrument provides a number of advantages for clinical diagnostic and therapeutic procedures in an MRI system, there are clinical applications wherein it is desirable to provide an MRI-compatible core sampling instrument that is not tethered, via a flexible driveshaft, to a control console. The driveshaft, although flexible, still imposes constraints due to its limited radius of bending. In addition, the drive shaft has an amount of inherent twist per length that creates a mechanical delay that may adversely impact closed-loop control, especially if a longer drive shaft is desired.

Another generally known approach to performing a core biopsy sampling is described in U.S. Pat. No. 6,758,824 wherein pneumatic pressure is used to turn a hydraulic rotary motor for cutter rotation and a hydraulic reciprocating actuator for cutter translation. While use of a remote pneumatic source connected through flexible pneumatic conduits is believed by some to be convenient and economical, such generally-known pneumatically-powered core biopsy systems do have some shortcomings.

An inherent issue with pneumatic drive motors is slow response time and inability to maintain a desired output shaft speed under loaded conditions. This phenomenon is associated with the compressibility of the gas that drives the system. In the case of a biopsy device containing a hollow cutter that rotates and translates, if dense tissue is encountered, the rotational speed of the pneumatically driven cutter may slow resulting in inconsistent tissue samples. And if the cutter is translated via a pneumatically driven piston-cylinder mechanism, the translation speed of the cutter may or may not change due to the density of the tissue. Therefore, the uncoordinated relationship between the cutter rotation speed and translation speed, coupled with the inherent poor response of the pneumatically driven cutter, often results in variations in the tissue sample weight when sampling heterogeneous tissue. It is believed that tissue sample weights are larger and more consistent when the number of rotations of the cutter through the aperture exceeds a minimum number of rotations.

Consequently, a significant need exists for a core biopsy device that is capable of use in proximity to an MRI machine as well as other imaging modalities yet avoids the inconveniences of being tethered by relatively long mechanical driveshafts as well as the inconsistent sample sizes produced by generally-known pneumatically-powered core sampling biopsy systems.

SUMMARY OF THE INVENTION

The present invention addresses these and other problems of the prior art by providing a core sampling biopsy system that is compatible with use proximate to a Magnetic Resonance Imaging (MRI) system yet does require a rotating mechanical drive shaft. Instead, a flexible power conduit powers a rotary nonferrous motor coupled to a biopsy handpiece.

In one aspect consistent with aspects of the invention, a biopsy device includes a rotary hydraulic drive motor that is coupled to a pressurized pneumatic source. The drive motor in turn drives a cutter drive assembly that rotates a cylindrical cutter down a cutter lumen at a fixed ratio to its longitudinal translation. It is understood that cutter rotations through the aperture are proportional to cutter rotation speed and inversely related to translation speed. Therefore the uncoordinated relationship between the cutter rotation speed and translation speed coupled with the inherent poor response of the pneumatically driven cutter can result in variations in the tissue sample weight when sampling heterogeneous tissue due to variations in cutter rotations through the aperture. However, the cutter drive assembly described below advantageously maintains a fixed relationship between the cutter rotation speed and translation speed at any speed based on the fixed gear ratios between the rotation drive shaft and translation drive shaft. For example, as the cutter rotation speed decreases, the cutter translation speed also decreases resulting in the same number of cutter rotations through the aperture. Likewise, as the cutter rotation speed increases, the cutter translation speed also increases resulting in the same number of cutter rotations through the aperture. Therefore, the inconsistent number of cutter rotations through the aperture associated with a pneumatically driven cutter is eliminated because the cutter drive assembly described below inherently maintains the number of cutter rotations through the aperture regardless of the density of the tissue encountered.

In another aspect of the invention, the fixed ratio cutter drive assembly is powered by a piezoelectric drive motor that is advantageously compatible with use near an MRI system.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

Pneumatic Biopsy Device

Figure 1:
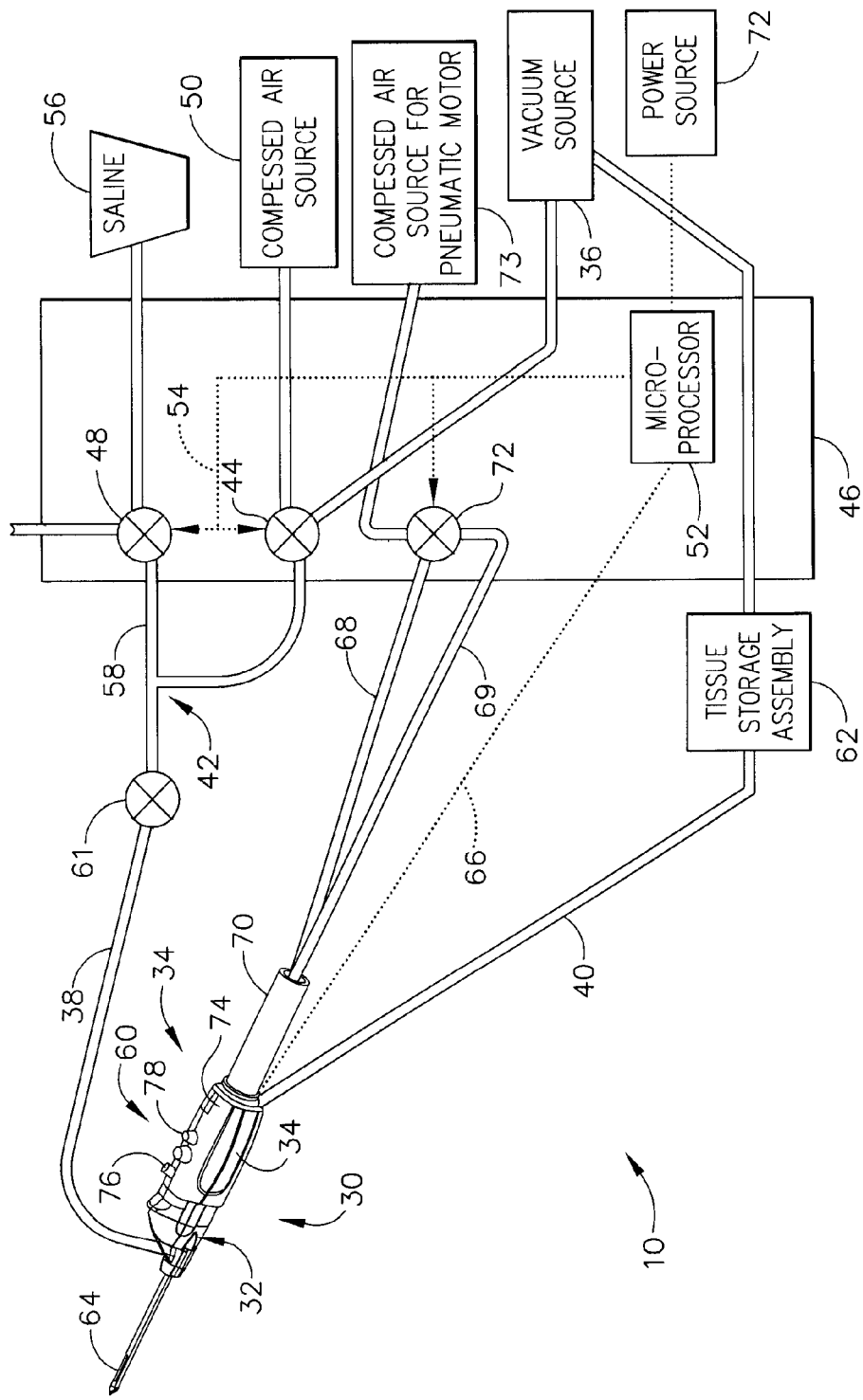
FIG. 1 is a partial isometric and partial schematic view of a core sampling biopsy system that includes a handpiece with a short stroke cutter that is advantageously pneumatically driven.

In FIG. 1, a pneumatic core sampling biopsy system 10 includes a handpiece 30 that may be held comfortably in a single hand, and may be manipulated with a single hand. Handpiece 30 may include a probe assembly 32 and a detachably connected holster 34. Probe assembly 32 may be operatively connected to a vacuum source 36, such as by a first, lateral tube 38 and a second, axial tube 40. First and second tubes 38, 40 may be made from a flexible, transparent or translucent material, such as silicon tubing, PVC tubing or polyethylene tubing. Using a transparent material enables visualization of the matter flowing through tubes 38, 40.

Figure 7:
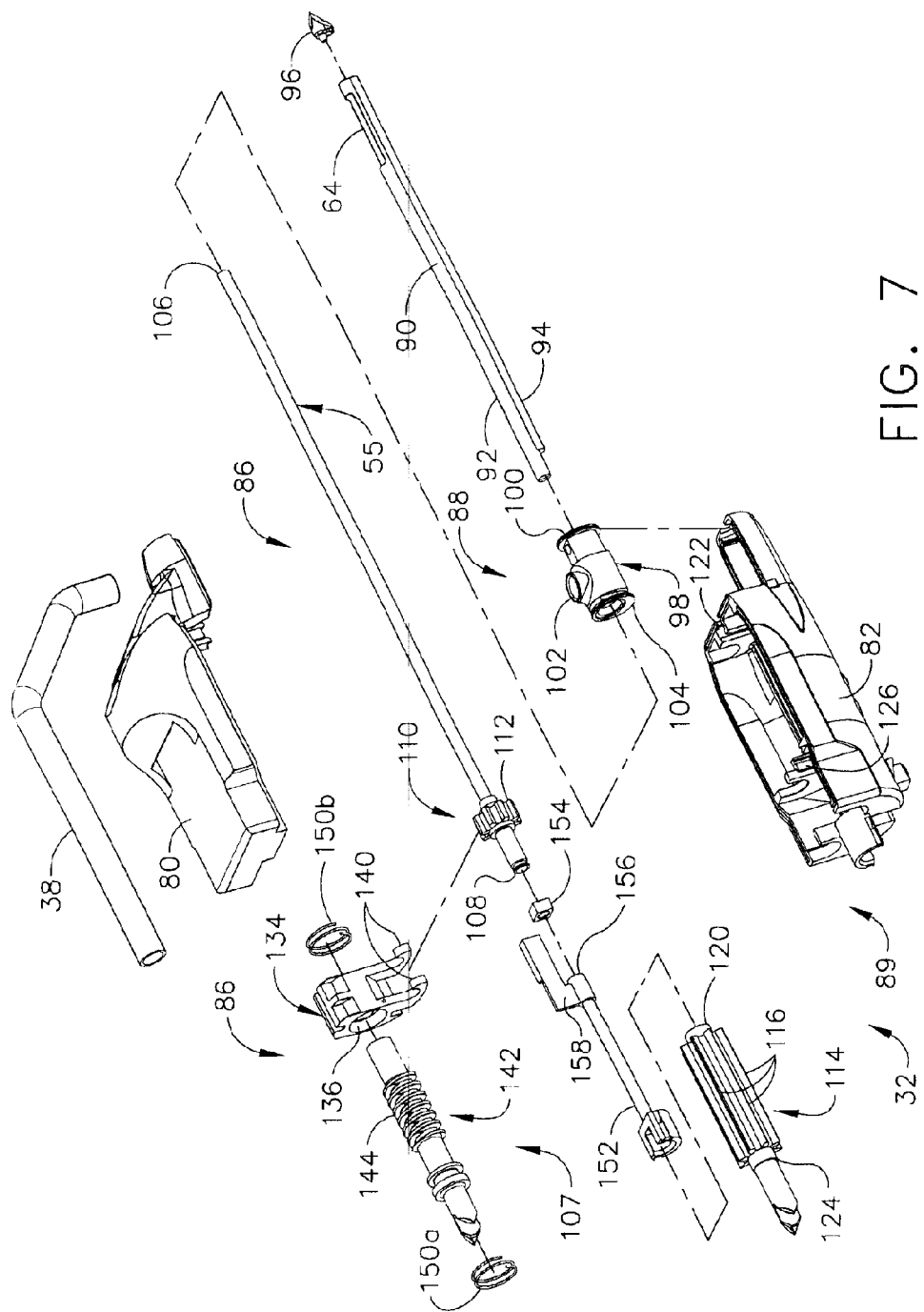
FIG. 7 is an exploded isometric view of the probe assembly of FIG. 3.

First tube 38 may include a Y connector 42 for connecting to multiple fluid sources. A first proximal end of Y connector 42 may extend to a first solenoid controlled rotary valve 44 in a control module 46, while the second proximal end of the Y connector 42 may extend to a second solenoid controlled rotary valve 48 in control module 46. The first solenoid controlled rotary valve 44 in control module 46 may be operable to connect either the vacuum source 36 or a compressed air source 50 to lateral tube 38. It is understood within this specification that compressed air means air pressure at or above atmospheric pressure. In one configuration, when valve 44 is activated, vacuum is supplied to tube 38 from vacuum source 36, and when valve 44 is not activated, pressurized air from compressed air source 50 is supplied through tube 38. The solenoid associated with valve 44 may be controlled by a microprocessor 52 in control module 46, as indicated by dashed line 54. The microprocessor 52 may be employed to adjust the position of valve 44 automatically based upon the position of a cutter 55 (as shown in FIG. 7) movably supported within probe assembly 32. The second solenoid controlled rotary valve 48 in control module 46 may be employed to either connect a saline supply 56 (such as a saline supply bag, or alternatively, a pressurized reservoir of saline) to a tube 58 or to seal off the proximal end of tube 58. For instance, rotary valve 48 may be activated by microprocessor 52 to supply saline when one of switches 60 on handpiece 30 is actuated. When rotary valve 48 is activated, first rotary valve 44 may be automatically deactivated (such as by microprocessor 52) to prevent the interaction of vacuum and saline within lateral tube 38. A stopcock 61 may be included in lateral vacuum tube 38 to allow for a syringe injection of saline directly into the tube 38, if desired. For instance, a syringe injection may be employed to increase the saline pressure in the tube to dislodge any clogs that may occur, such as tissue clogging fluid passageways.

In one version, axial vacuum tube 40 may be employed to communicate vacuum from source 36 to probe assembly 32 through a tissue storage assembly 62. Axial tube 40 may provide vacuum through the cutter 55 within probe assembly 32 to assist in prolapsing tissue into a side aperture 64 prior to cutting. After cutting occurs, the vacuum in axial tube 40 may be employed to help draw a severed tissue sample from probe assembly 32 and into tissue storage assembly 62. Holster 34 may include a control cord 66 for operationally connecting handpiece 30 to control module 46.

A pneumatic drive motor 70 advantageously replaces a rotatable drive cable used in generally-known MRI-compatible core sampling biopsy systems. The pneumatic drive motor 70 would be located proximal of the handpiece 30. The pneumatic drive motor 70 has two pneumatic input lines 68 and 69. When compressed gas is applied to one of the two lines 68, 69, the output shaft (not shown) of pneumatic drive motor 70 rotates in a given direction. When compressed gas is applied to the other line 69, 68, the output shaft of the pneumatic drive motor 70 rotates in the opposite direction. In each case, the pneumatic input line 68, 69 that does not carry the compressed gas is the exhaust or vent line for the compressed gas. This switching between OFF/Input 1 ON and Input 2 Vent/Input 1 Vent and Input 2 ON may be accomplished by microprocessor 52 commanding a pneumatic switching valve 72 that receives compressed air from a source 73 and selectively switches the compressed air to pneumatic input lines 68, 69. The compressed gas rotates the output shaft of the pneumatic drive motor 70 via a rotor blade assembly (not shown). The output shaft of the pneumatic drive motor 70 then drives the input shaft of a cutter drive assembly (not shown in FIG. 1).

An example of a pneumatic drive motor 70 is available from Pro-Dex Micro Motors Inc. model MMR-0700.

Switches 60 are mounted on holster upper shell 74 to enable an operator to use handpiece 30 with a single hand. One-handed operation allows the operator's other hand to be free, for example, to hold an ultrasonic imaging device. Switches 60 may include a two-position rocker switch 76 for manually actuating the motion of the cutter 55 (e.g. forward movement of the rocker switch 76 moves the cutter 55 in the forward (distal) direction for tissue sampling and rearward movement of the rocker switch 76 actuates the cutter 55 in the reverse (proximal) direction). Alternatively, the cutter 55 could be automatically actuated by control module 46. An additional switch 78 may be provided on holster 34 for permitting the operator to activate saline flow on demand into lateral tube 38 (for instance, switch 78 may be configured to operate valve 48 for providing saline flow to tube 38 when switch 78 is depressed by the user).

As an alternate configuration, it should be noted that the pneumatic drive motor drive assembly described herein could rotate and translate a cutter within biopsy devices where the cutter translates the entire length of the needle to extract the tissue from the patient.

Piezoelectric Motor-Drive Core Sampling Biopsy System.

Figure 2:
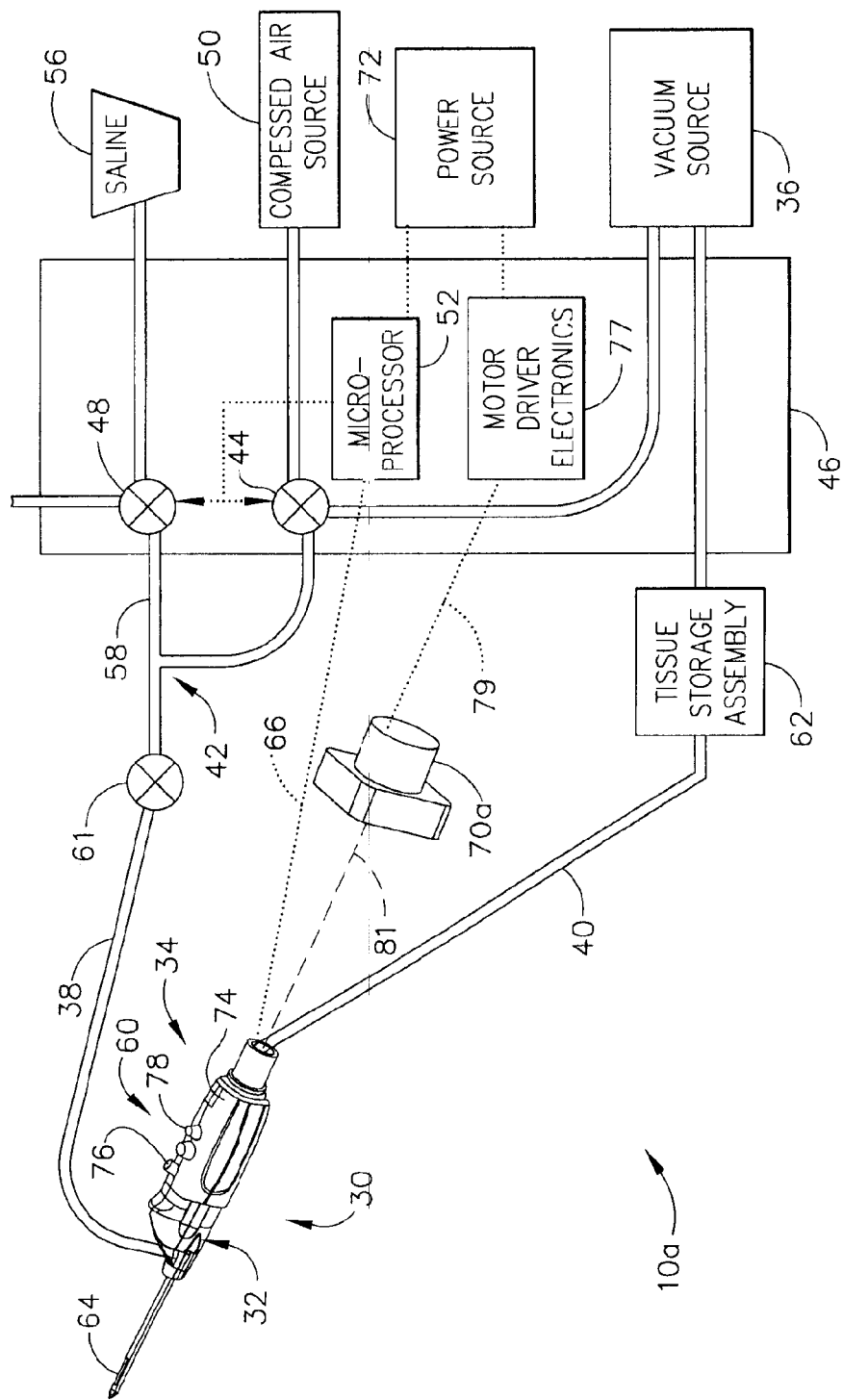
FIG. 2 is a partial isometric and partial schematic view of a core sampling biopsy system that includes a handpiece with a short stroke cutter that is advantageously piezoelectrically driven.

In FIG. 2, a piezoelectrically-driven biopsy system 10a is similar to that described above for FIG. 1 but includes some changes. In particular, a piezoelectric motor 70a is advantageously completely or partially replacing a generally known mechanical rotatable drive cable. The piezoelectric drive motor 70a may be located immediately proximal of the cutter drive assembly (not shown in FIG. 2). The piezoelectric drive motor 70a is driven by motor driver circuitry 77, which is powered by power source 72, via electrical cable 79. It should be appreciated that the motion of a piezoelectric crystal material rotates a rotor attached to the output shaft (not shown) of the piezoelectric drive motor 70a. The output shaft of the piezoelectric drive motor 70a then drives the input shaft of the cutter drive assembly. An example of a piezoelectric drive motor 70a is available from Shinsei Corporation drive motor model USR 10-E3N and electronic driver model D6060.

A design aspect of current piezoelectric motors is the low power density of the motors. This results in piezoelectric motors with a relatively large volume when compared to conventional DC motors at a given power rating. In the event the piezoelectric drive motor 70a is too large to be attached directly to the input shaft of the cutter drive assembly 107 FIG. 4, the output of the piezoelectric drive motor 70a may drive a rotatable drive cable 81. This would allow the piezoelectric drive motor 70a to be located some distance from the holster to reduce the holster mass. As an additional alternate configuration, one piezoelectric motor could rotate the cutter assembly and a second piezoelectric motor could translate the cutter assembly. Piezoelectric motors are particularly suited for MRI applications based on their material properties. It should be noted that the piezoelectric motor drive assembly described herein could rotate and translate a cutter within biopsy devices where the cutter translates the entire length of the needle to extract the tissue from the patient.

Short Stroke Cutter Drive Assembly.

Figure 3:
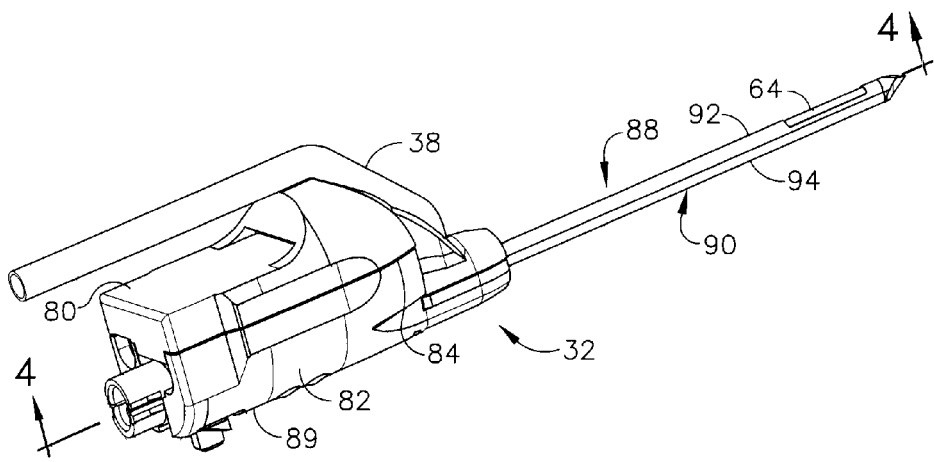
FIG. 3 is an isometric view of a probe assembly of the handpiece of FIG. 1 with a holster removed.

With the pneumatic drive motor 70 of FIG. 1 or the alternative piezoelectric drive motor 70a of FIG. 2 omitted, the components of the handpiece 30 will now be described. FIG. 3 shows probe assembly 32 disconnected from holster 34. Probe assembly 32 includes an upper shell 80 and a lower shell 82, each of which may be injection molded from a rigid, biocompatible plastic, such as a polycarbonate. Upon final assembly of probe assembly 32, upper and lower shells 80, 82 may be joined together along a joining edge 84 by any of a number of methods well known for joining plastic parts, including, without limitation, ultrasonic welding, snap fasteners, interference fit, and adhesive joining.

Figure 4:
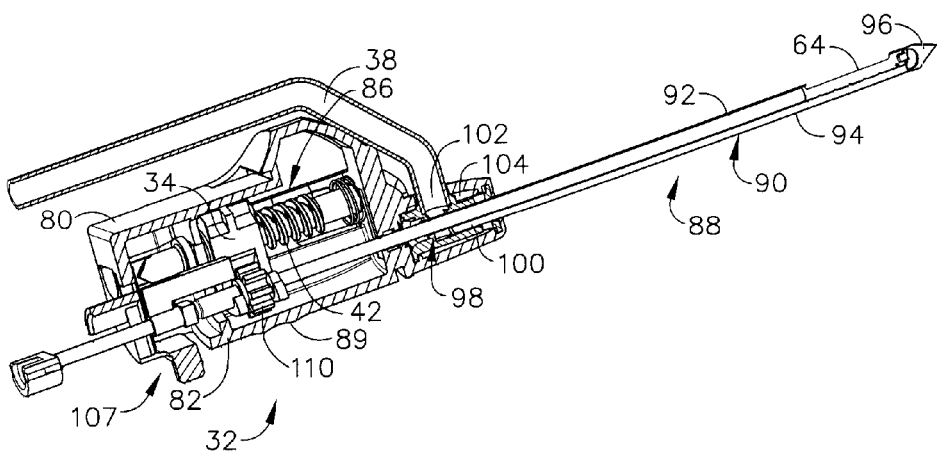
FIG. 4 is a cross sectional isometric view of the probe assembly of FIG. 3 taken along line 4-4 with a cutter and carriage assembly positioned at a proximal position.
Figure 5:
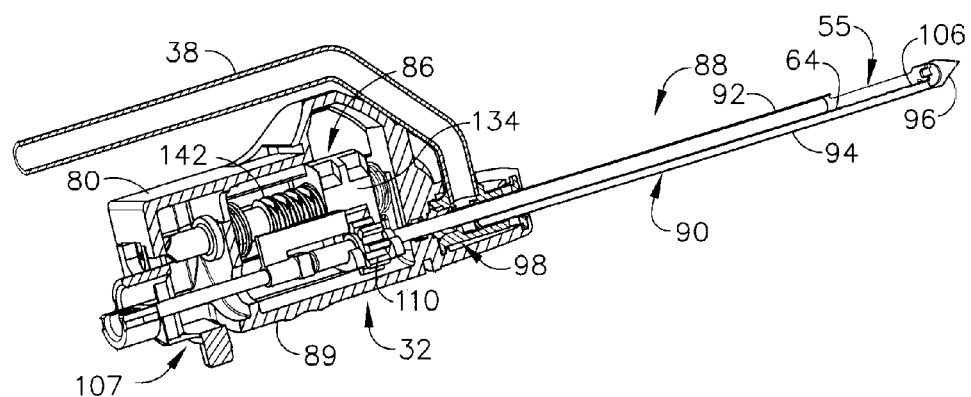
FIG. 5 is a cross-sectional isometric view of the probe assembly of FIG. 3 taken along line 4-4 with the cutter and carriage assembly positioned between proximal and distal end positions.
Figure 6:
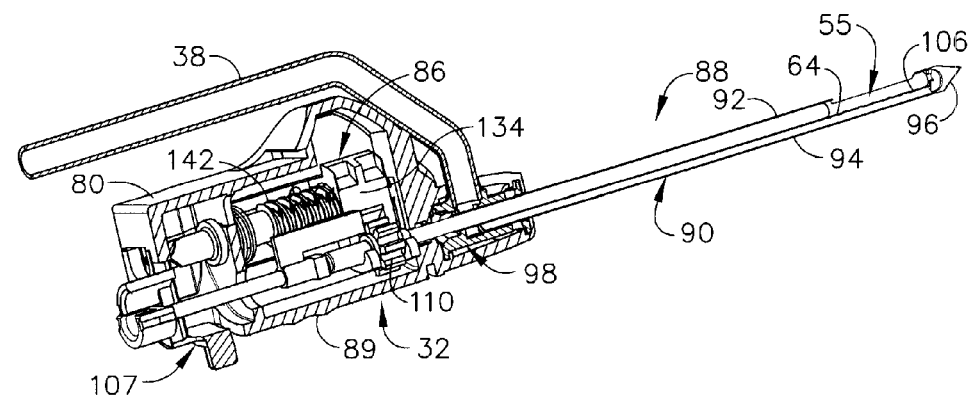
FIG. 6 is a cross-sectional isometric view of the probe assembly of FIG. 3 taken along line 4-4 with the cutter and carriage assembly positioned at the distal end position.

FIGS. 4-7 illustrate probe assembly 32 in greater detail. FIG. 4 depicts a cutter assembly and carriage 86 retracted proximally. FIG. 5 depicts the cutter assembly and carriage 86 partially advanced. FIG. 6 depicts the cutter assembly and carriage 86 advanced distally. With particular reference to FIG. 7, the probe assembly 32 may include a biopsy needle (probe) 88 located at a distal end of a handle 89 of the probe assembly 32 for insertion into a patient's skin to obtain a tissue sample. Needle 88 comprises an elongated, metallic cannula 90, which may include an upper cutter lumen 92 for receiving the cutter 55 and a lower vacuum lumen 94 for providing a fluid and pneumatic passageway. Cutter 55 may be disposed within cannula 90, and may be coaxially disposed within cutter lumen 92.

Cannula 90 may have any suitable cross-sectional shape, including a circular or oval shaped cross-section. Adjacent and proximal of the distal end of cannula 90 is the side (lateral) tissue receiving port (side aperture) 64 for receiving the tissue to be severed from the patient. The sharpened tip of needle 88 may be formed by a separate endpiece 96 attached to the distal end of cannula 90. The sharpened tip of endpiece 96 may be used to pierce the patient's skin so that the side tissue receiving port may be positioned in the tissue mass to be sampled. Endpiece 96 may have a two-sided, flat-shaped point as shown, or any number of other shapes suitable for penetrating the soft tissue of the patient.

The proximal end of needle 88 may be attached to a union sleeve 98 having a longitudinal bore 100 therethrough, and a transverse opening 102 into a widened center portion of the bore 100. The distal end of lateral tube 38 may be inserted to fit tightly into transverse opening 102 of union sleeve 98. This attachment allows the communication of fluids (gas or liquid) between the lower vacuum lumen 94 and the lateral tube 38.

The cutter 55, which may be an elongated, tubular cutter, may be disposed at least partially within upper cutter lumen 92, and may be supported for translation and rotation within cutter lumen 92. Cutter 55 may be supported within vacuum lumen 94 so as to be translatable in both the distal and proximal directions. Cutter 55 may have a sharpened distal end 106 for cutting tissue received in upper cutter lumen 92 through side tissue receiving port 64. The cutter 55 may be formed of any suitable material, including without limitation a metal, a polymer, a ceramic, or a combination of materials. Cutter 55 may be translated within cutter lumen 92 by a suitable cutter drive assembly 107 such that distal end 106 travels from a position proximal of the side tissue port 64 (illustrated in FIG. 4) to a position distal of side tissue port 64 (illustrated in FIG. 6), in order to cut tissue received in cutter lumen 92 through the side tissue port 64. In an alternative embodiment, an exterior cutter (not shown) may be employed, with the exterior cutter sliding coaxially with an inner cannular needle, and the inner needle may include a side tissue receiving port.

Union sleeve 98 is supported between probe upper and lower shells 80, 82 to ensure proper alignment between cutter 55 and the union sleeve 98. The cutter 55 may be a hollow tube, with a sample lumen 108 extending axially through the length of cutter 55. The proximal end of cutter 55 may extend through an axial bore of a cutter gear 110. Cutter gear 110 may be metallic or polymeric, and includes a plurality of cutter gear teeth 112. Cutter gear 110 may be driven by a rotary drive shaft 114 having a plurality of drive gear teeth 116 designed to mesh with cutter gear teeth 112. Drive gear teeth 116 may extend along the length of drive shaft 114 so as to engage cutter gear teeth 112 as the cutter 55 translates from a proximal most position to a distal most position, as illustrated in FIGS. 4-6. Drive gear teeth 116 may be in continual engagement with cutter gear teeth 112 to rotate cutter 55 whenever drive shaft 114 is rotatably driven. Drive shaft 114 rotates cutter 55 as the cutter advances distally through tissue receiving port 64 for the cutting of tissue. Drive shaft 114 may be injection molded from a rigid engineered plastic such as liquid crystal polymer material or, alternatively, could be manufactured from a metallic or non-metallic material. Drive shaft 114 includes a first axial end 120 extending distally from the shaft 114. Axial end 120 is supported for rotation within probe lower shell 82, such as by a bearing surface feature 122 molded on the inside of the probe shells 80, 82. Similarly, a second axial end 124 extends proximally from rotary drive shaft 114 and is supported in a second bearing surface feature 126, which may also be molded on the inside of probe lower shell 82. An O-ring and bushing (not shown) may be provided on each axial end 120, 124 to provide rotational support and audible noise dampening of the shaft 114 when rotary drive shaft 114 is mounted in probe lower shell 82.

As shown in FIGS. 4-6, a drive carriage 134 is provided in probe assembly 32 to hold cutter gear 110, and carry the cutter gear and attached cutter 55 during translation in both the distal and proximal directions. Drive carriage 134 may be molded from a rigid polymer and has a cylindrically-shaped bore 136 extending axially therethrough. A pair of J-shaped hook extensions 140 extend from one side of drive carriage 134. Hook extensions 140 rotatably support cutter 55 on either side of cutter gear 110 to provide proximal and distal translation of the cutter gear 110 and cutter 55 during proximal and distal translation of drive carriage 134. Hook extensions 140 align cutter 55 and cutter gear 110 in the proper orientation for cutter gear teeth 112 to mesh with drive gear teeth 116.

Drive carriage 134 is supported on a translation shaft 142. Shaft 142 is supported generally parallel to cutter 55 and rotary drive shaft 114. Rotation of the translation shaft 142 provides translation of the drive carriage 134 (and thus also cutter gear 110 and cutter 55) by employing a lead screw type drive. Shaft 142 includes an external lead screw thread feature, such as lead screw thread 144, on its outer surface. The screw thread 144 extends into the bore 136 in drive carriage 134. The screw thread 144 engages an internal helical threaded surface feature (not shown) provided on the inner surface of bore 136. Accordingly, as shaft 142 is rotated, the drive carriage 134 translates along the threaded feature 144 of the shaft 142. The cutter gear 110 and the cutter 55 translate with the drive carriage 134. Reversing the direction of rotation of shaft 142 reverses the direction of translation of the drive carriage 134 and the cutter 55. Translation shaft 142 may be injection molded from a rigid engineered plastic such as liquid crystal polymer material or, alternatively, could be manufactured from a metallic or non-metallic material. Translation shaft 142 with lead screw thread feature 144 may be molded, machined, or otherwise formed. Likewise, drive carriage 134 may be molded or machined to include an internal helical thread in bore 136. Rotation of shaft 142 drives the carriage and cutter gear 110 and cutter 55 in the distal and proximal directions, depending upon the direction of rotation of shaft 142, so that cutter 55 translates within probe assembly 32. Cutter gear 110 is rigidly attached to cutter 55 so that the cutter translates in the same direction and at the same speed as drive carriage 134.

In one version, at the distal and proximal ends of lead screw thread 144, the helical thread is cut short so that the effective pitch width of the thread is zero. At these distal most and proximal most positions of thread 144, translation of drive carriage 134 is no longer positively driven by shaft 142 regardless of the continued rotation of shaft 142, as the carriage effectively runs off the thread 144. Biasing members, such as compression coil springs 150a and 150b (FIG. 7), are positioned on shaft 142 adjacent the distal and proximal ends of the screw thread 144. Springs 150a-b bias drive carriage 134 back into engagement with lead screw thread 144 when the carriage runs off the thread 144. While shaft 142 continues rotating in the same direction, the zero pitch width thread in combination with springs 150a-b cause drive carriage 134 and, therefore, cutter 55 to "freewheel" at the end of the shaft. At the proximal end of the threaded portion of shaft 142, the drive carriage 134 engages spring 150a. At the distal end of the threaded portion of shaft 142, the drive carriage 134 engages spring 150b. When the drive carriage 134 runs off the screw thread 144, the spring 150a or 150b engages the drive carriage 134 and biases the drive carriage 134 back into engagement with the screw thread 144 of shaft 142, at which point continued rotation of the shaft 142 again causes the drive carriage 134 to run off the screw thread 144. Accordingly, as long as rotation of shaft 142 is maintained in the same direction, the drive carriage 134 (and cutter 55) will continue to "freewheel", with the distal end of the cutter 55 translating a short distance proximally and distally as the carriage is alternately biased onto the thread 144 by spring 150a or 150b and then run off the screw thread 144 by rotation of shaft 142. When the cutter is in the distal most position shown in FIG. 6, with the distal end 106 of the cutter 55 positioned distal of side tissue port 64, spring 150b will engage drive carriage 134, and repeatedly urge drive carriage 134 back into engagement with screw thread 144 when drive carriage 134 runs off the screw thread 144. Accordingly, after the cutter 55 is advanced such that the distal end 106 of the cutter 55 translates distally past the side tissue port 64 to cut tissue, to the position shown in FIG. 6, continued rotation of the shaft 142 will result in the distal end 106 oscillating back and forth, translating a short distance proximally and distally, until the direction of rotation of shaft 142 is reversed (such as to retract the cutter 55 distally to the position shown in FIG. 4). With the cutter 55 in its distal most position shown in FIG. 6, the slight movement of drive carriage 134 into engagement with the screw thread 144 and out of engagement with the screw thread 144 against the biasing force of spring 150b, causes the distal end 106 of cutter 55 to repetitively reciprocate a short distance within cannula 90, which distance may be about equal to the pitch of threads 144, and which distance is shorter than the distance the cutter travels in crossing the side tissue port 64. This reciprocal movement of the cutter 55 may provide alternate covering and uncovering of at least one fluid passageway disposed distally of the side tissue port 64, as described below.

The zero pitch width ends of lead screw thread 144 provide a defined stop for the axial translation of cutter 55, thereby eliminating the need to slow drive carriage 134 (i.e. cutter 55) as it approaches the distal and proximal ends of the thread.

This defined stop reduces the required positioning accuracy for drive carriage 134 relative to shaft 142, resulting in reduced calibration time at the initialization of a procedure. The freewheeling of drive carriage 134 at the distal and proximal most positions of translation shaft 142 eliminates the need to rotate the shaft 142 a precise number of turns during a procedure. Rather, translation shaft 142 only needs to translate at least a minimum number of turns to insure drive carriage 134 has translated the entire length of lead screw thread 144 and into the zero width thread. Additionally, the freewheeling of drive carriage 134 eliminates the need to home the device, allowing probe assembly 32 to be inserted into the patient's tissue without first being attached to holster 34. After probe assembly 32 is inserted, holster 34 is attached and sampling may be commenced.

As shown in FIG. 7, a non-rotating rear tube 152 may be provided in which tube 152 may extend from the proximal end of cutter 55 just proximal of cutter gear 110. Rear tube 152 may be hollow and may have substantially the same inner diameter as cutter 55, and may be comprised of the same material as the cutter 55. A seal 154 may be positioned between cutter 55 and rear tube 152 to enable the cutter 55 to rotate relative to the rear tube 152 while providing a pneumatic seal between the rear tube 152 and the cutter 55. A rear lumen 156 may extend through the length of tube 152 and may be aligned with sample lumen 108 in cutter 55. Rear lumen 156 transports excised tissue samples from sample lumen 108 through probe assembly 32 to the tissue storage assembly 62. Sample lumen 108 and rear lumen 156 are axially aligned to provide a continuous, generally straight line, unobstructed passageway between tissue receiving port 64 and tissue storage assembly 62 for the transport of tissue samples. The inner surfaces of cutter 55 and tube 152 may be coated with a hydrolubricous material to aid in the proximal transport of the excised tissue samples.

A lateral extension 158 may be supported by and extend distally from rear tube 152 for securing the tube 152 to drive carriage 134. The extension 158 connects tube 152 to drive carriage 134 so that tube 152 translates with cutter 55, and maintains lumens 108, 156 in continuous fluid-tight communication throughout the cutting cycle.

Single Input-Dual Output Holster Gearbox Assembly.

Figure 8:
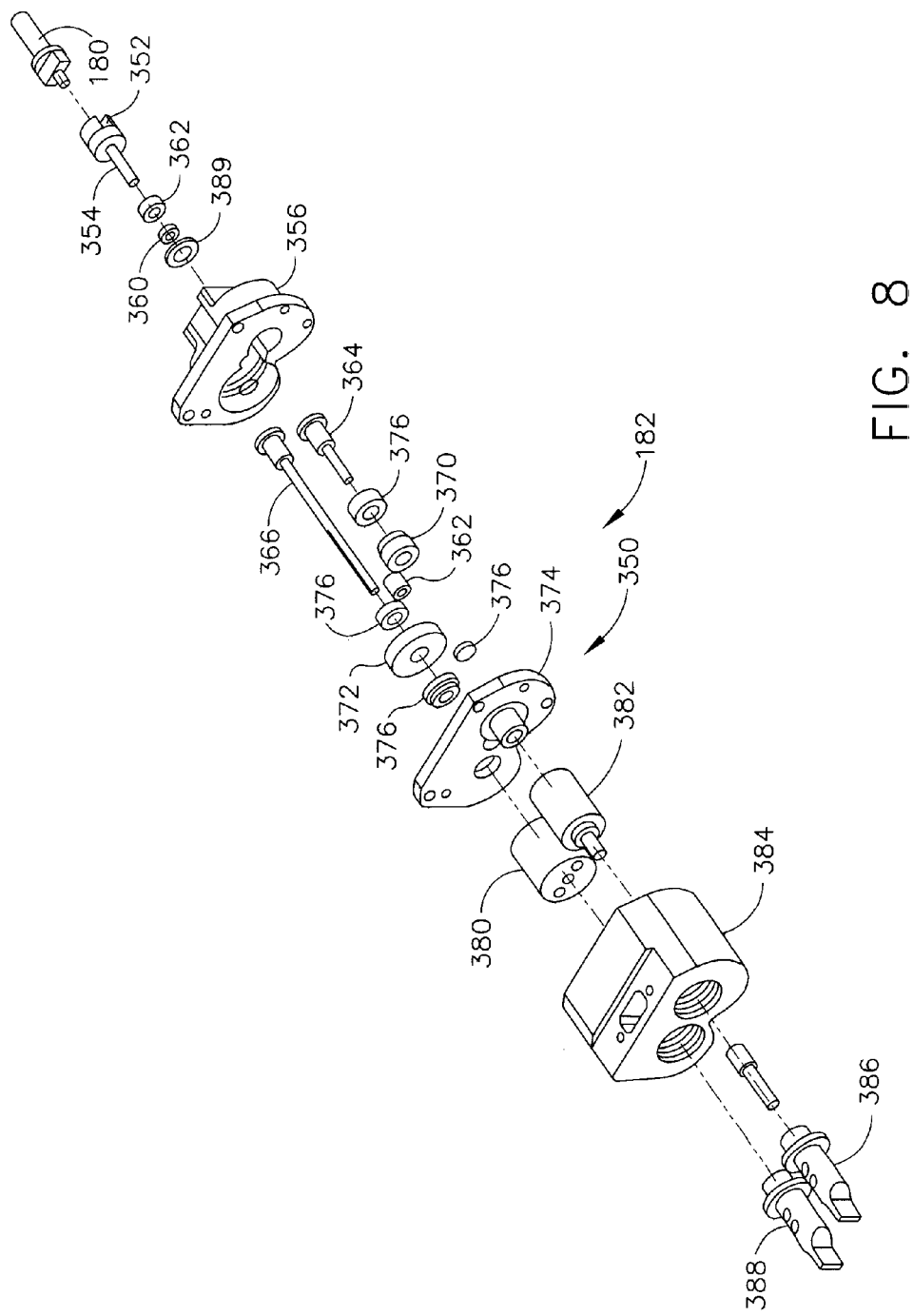
FIG. 8 is an exploded isometric view of a single input-dual output driven drive assembly for the holster of FIGS. 1-2, viewed in the proximal direction.

In FIG. 8, the rotary drive shaft 114 and translation shaft 142 are driven by a single drive input 180 via a single rotatable input 55 (also shown in FIG. 1) via a holster gearbox assembly 182. The single drive input 180 is driven in turn by either the pneumatic drive motor 70 (FIG. 1) or the piezoelectric motor 70a (FIG. 2). Rotatable drive input 180 attaches to a drive cable input coupling 352 for providing rotational drive to holster 34. A drive shaft 354 from input coupling 352 extends to a proximal housing 356. Within proximal housing 356, an input gear 360 is mounted on input drive shaft 354 between spacer 362 and bearing 389 so as to engage corresponding gears on a translation drive shaft 364 and a rotation drive shaft 366. The interaction of the input gear 360 with translation shaft gear 370 and rotation shaft gear 372 transmits the rotational drive to translation and rotation drive shafts 364, 366. Translation and rotation drive shafts 364, 366 extend from proximal housing 356 through a pair of bores in a center housing 374. Translation and rotation gears 370, 372 are spaced between the proximal and center housings by bearings 376.

Distal of center housing 374, holster 34 includes a rotary encoder 380 for providing a feedback signal to control module 46 regarding rotation of the drive shafts. Encoder 380 may be mounted on either the translation or the rotation drive shafts. Holster 34 also includes an optional planetary gearbox 382 on translation drive shaft 364. Gearbox 382 provides a gear reduction between the rotary drive shaft 114 and translation shaft 142 to produce differing speeds for the translation of drive carriage 134 and the rotation of cutter 55. Distal of gearbox 382 and encoder 380, drive assembly 350 includes a housing 384. Housing 384 includes connections for coupling the translation shaft 142 with translation drive input shaft 386, and the rotational drive shaft 114 with rotary drive input shaft 388. Each of the drive input shafts 386, 388 has a distal end shaped to operatively engage slots on corresponding drive shafts 114, 142 in probe assembly 32. In particular, translation drive input shaft 386 is shaped to engage a slot of translation shaft 142 (shown in FIG. 7), and rotary drive input shaft 388 is shaped to engage a slot of rotary drive shaft 114. Alternatively, drive input shafts may have molded interfaces rather than the mating slots and tips as shown in FIGS. 7 and 8 to reduce the coupling length between the shafts. Translation and rotary drive shafts 386, 388 extend distally from housing 384 for engagement with drive and translation shafts 114, 142 when probe assembly 32 and holster 34 are connected.

While illustrative versions of the present invention have been shown and described herein, it will be obvious to those skilled in the art that such embodiments are provided by way of example only. Numerous variations, changes, and substitutions will now occur to those skilled in the art without departing from the spirit and scope of the appended claims. Additionally, each element described in relation to the invention may be alternatively described as a means for performing that element's function.

For example, while a microprocessor control console 46 is advantageously described, it should be appreciated that an alternate control approach may be employed. For instance, switchology on a handpiece may activate pneumatic valves to cause rotation and translation. For instance, a single pneumatic input line to the handpiece may be manually switched at the handpiece to a rotary motor to achieve one of three conditions: Off, Clockwise, and Counterclockwise.

For another example, a core sampling biopsy system as described in U.S. Pat. No. 6,273,862 that performs a long cutting stroke to take samples and to retract them from the probe may also advantageously benefit from an MRI-compatible power source (e.g., pneumatic, piezoelectric) as described herein.

For a further example, while vacuum assist is advantageously described herein to assist in functions such as prolapsing tissue and retracting samples through the probe, it should be appreciated that applications consistent with the present invention would benefit from pneumatic or piezoelectric driven biopsy devices.

For yet a further example, while a version described herein illustrates compressed air to drive a cutter drive assembly, it should be appreciated that a incompressible fluid may be used in applications consistent with aspects of the present invention.

For yet a further example, while a version described herein illustrates compressed air to drive a cutter drive assembly, it should be appreciated that vacuum may be used to drive the pneumatic motor to then drive the cutter drive assembly, in applications consistent with aspects of the present invention.

What is claimed is:

1. A biopsy device, comprising:
   a. an outer piercing tube having an aperture proximate to a distal end thereof for receiving prolapsed tissue, wherein the outer piercing tube has a sharpened closed tip configured to penetrate a patient's skin;
   b. a cutter tube longitudinally translatable within the piercing tube;
   c. a cutter drive assembly comprising:
      (i) a translation drive shaft operable to translate the cutter tube,
      (ii) a rotation drive shaft operable to rotate the cutter tube, and
      (iii) a single-input to dual-output gearbox assembly coupled with the translation drive shaft and the rotation drive shaft, wherein the single-input to dual-output gearbox assembly comprises a translation gear coupled with the translation drive shaft, a rotation gear coupled with the rotation drive shaft, and a common input gear coupled with both the translation gear and the rotation gear, wherein the gearbox assembly is configured to rotate the translation gear and the rotation gear simultaneously in response to rotation of the common input gear;
   wherein the cutter drive assembly is operatively configured to:
      (v) distally translate the cutter tube at a rate of translation and rotate the cutter tube at a rate of rotation, wherein the rate of translation is in constant proportion to the rate of rotation,
      (vi) rotate the cutter tube through a predetermined number of rotations of the cutter tube across the aperture severing received prolapsed tissue,
      (vii) maintain the predetermined number of rotations despite axial resistance encountered by the cutter tube from tissues of varying density, and
      (viii) translate the cutter tube at a variable rate, wherein the predetermined number of rotations remains constant despite variations in the cutter tube rate of translation; and
   d. a rotary motor coupled to the common input gear, such that the rotary motor is operable to rotate the common input gear of the cutter drive assembly.

2. The biopsy device of claim 1, wherein the rotary motor comprises a hydraulic rotary motor.

3. The biopsy device of claim 2, wherein the hydraulic rotary motor comprises a pneumatic rotary motor.

4. The biopsy device of claim 1, further comprising a vacuum assist assembly selectively communicated to the cutter tube to effect prolapse of tissue.

5. The biopsy device of claim 4, further comprising a vacuum lumen communicating between a distal end of the cutter tube and the vacuum assist assembly.

6. The biopsy device of claim 1, wherein the rotary motor comprises a piezoelectric rotary motor.

7. The biopsy device of claim 6, further comprising a flexible drive shaft coupling the piezoelectric rotary motor to the cutter drive assembly.

8. The biopsy device of claim 1, wherein the rotary motor coupled to the common input gear of the cutter drive assembly comprises a nonferrous rotary motor.

9. A biopsy device, comprising:
   a. a piercing tube having an aperture proximate to a distal end thereof for receiving prolapsed tissue;
   b. a cutter tube longitudinally translatable within the piercing tube;
   c. a cutter drive assembly comprising:
      (i) a first rotatable drive shaft configured to cause the cutter tube to translate, wherein the first rotatable drive shaft is coupled with a first gear,
      (ii) a second rotatable drive shaft configured to cause the cutter tube to rotate, wherein the second rotatable drive shaft is coupled with a second gear, and
      (iii) a common input gear, wherein the first gear and the second gear are coupled with the common input gear,
   wherein the cutter drive assembly is operatively configured to:
      (iv) distally translate the cutter tube at a rate of translation and rotate the cutter tube at a rate of rotation, wherein the rate of translation is in constant proportion to the rate of rotation,
      (v) rotate the cutter tube through a predetermined number of rotations of the cutter tube across the aperture to sever prolapsed tissue,
      (vi) maintain the predetermined number of rotations despite axial resistance encountered by the cutter tube from tissues of varying density,
      (vii) translate the cutter tube at a variable rate; and
   d. a rotary motor coupled with the common input gear of the cutter drive assembly.

10. The biopsy device of claim 9, further comprising a vacuum assist assembly selectively communicated to the cutter tube to effect prolapse of tissue.

11. The biopsy device of claim 10, further comprising a vacuum lumen communicating between a distal end of the cutter tube and the vacuum assist assembly.

12. The biopsy device of claim 9, wherein the cutter drive assembly further comprises a single-input to dual-output gearbox housing the first gear, the second gear, and the common input gear.

13. A biopsy device, comprising:
   a. a piercing tube having an aperture proximate to a distal end thereof for receiving prolapsed tissue;
   b. a cutter tube longitudinally translatable within the piercing tube;
   c. a cutter drive assembly comprising:
      (i) a threaded drive member operable to translate the cutter tube, wherein the threaded drive member comprises a first thread region having a non-zero pitch, wherein the threaded drive member further comprises a distal thread region having a zero pitch, wherein the zero pitch of the distal thread region permits the cutter tube to rotate through at least one full revolution without translating,
      (ii) a rotational drive member operable to rotate the cutter tube,
      (iii) a rotary motor, and
      (iv) a single-input to dual-output gearbox assembly coupling the rotary motor with the threaded drive member and the rotational drive member, wherein the gearbox assembly comprises:
         (A) a translation gear coupled with the threaded drive member,
         (B) a rotation gear coupled with the rotational drive member, (C) a common input gear, wherein the translation gear and rotation gear are coupled with the common input gear, wherein the common input gear is in further communication with the rotary motor, wherein the cutter drive assembly is operably configured to:
(v) distally translate the cutter tube at a rate of translation and rotate the cutter tube at a rate of rotation, wherein the rate of translation is in constant proportion to the rate of rotation, and
(vi) rotate the cutter tube through a predetermined number of rotations of the cutter tube across the aperture severing prolapsed tissue.

14. The biopsy device of claim 13, further comprising a vacuum assist assembly selectively communicated to the cutter tube to effect prolapse of tissue.

15. The biopsy device of claim 14, further comprising a vacuum lumen communicating between a distal end of the cutter tube and the vacuum assist assembly.

16. The biopsy device of claim 14, further comprising a flexible drive shaft coupling the rotary motor to the common input gear.

* * * * *